(12) United States Patent
Proudfoot et al.

(10) Patent No.: US 6,555,105 B1
(45) Date of Patent: *Apr. 29, 2003

(54) METHOD OF TREATMENT WITH A RANTES ANTAGONIST POLYPEPTIDE

(75) Inventors: Amanda E. I. Proudfoot, Geneva (CH); Timothy N. C. Wells, Geneva (CH)

(73) Assignee: Glaxo Group Limited, Middlesex (GB)

( * ) Notice: Subject to any disclaimer, the term of this patent is extended or adjusted under 35 U.S.C. 154(b) by 8 days.

This patent is subject to a terminal disclaimer.

(21) Appl. No.: 09/639,881

(22) Filed: Aug. 17, 2000

Related U.S. Application Data

(63) Continuation of application No. 08/836,922, filed as application No. PCT/GB95/02861 on Dec. 7, 1995, now Pat. No. 6,159,711.

(30) Foreign Application Priority Data

Dec. 8, 1994 (GB) ............................................... 9424835
Jun. 16, 1995 (GB) ............................................... 9512319

(51) Int. Cl.⁷ ............................................... A61K 38/19
(52) U.S. Cl. ............................... 424/85.1; 514/2; 514/8; 514/12; 514/824; 514/825; 514/826; 514/885; 514/886
(58) Field of Search .................. 514/2, 8, 12, 885, 514/886, 826, 824, 825; 424/85.1

(56) References Cited

U.S. PATENT DOCUMENTS 6,159,711 A * 12/2000 Proudfoot et al. ......... 435/69.5

OTHER PUBLICATIONS

Zhang et al, "Structure/Activity Analysis of Human Monocyte Chemoattractant Protein–1 (MCP–1) by Mutagenesis", Journal of Biological Chemistry 269(22):15918–15924 (1994).

Gong and Clark–Lewis, "Antagonists of Monocyte Chemoattractant Protein–1 Identified by Modification of Functionally Critical NH–2 terminal Residues", Journal of Experimental Medicine 181:631–640 (1995).

Herbert et al, "Scanning Mutagenesis of Interleukin–8 Identifies a Cluster of Residues Required for Receptor Binding", 266(28):18989–18994 (1991).

Moser et al, "Interleukin–8 Antagonists Generated by N–terminal Modification", Journal of Biological Chemistry 268(10):7125–7128 (1993).

Cunningham et al, "High–Resolution Epitope Mapping of hGH–Receptor Interactions by Alanine–Scanning Mutagenesis", Science 266:1081–1085 (1989).

George et al, "Current Methods in Sequence Comparison and Analysis", Macromolecular Sequencing and Synthesis Selected Methods and Applications, Chapter 12, pp. 127–149 (1988)—Alan R. Liss, Inc., New York.

\* cited by examiner

*Primary Examiner*—Prema Mertz
(74) *Attorney, Agent, or Firm*—Nixon & Vanderhye P.C.

(57) ABSTRACT

Modifications to RANTES can result in the modified polypeptide acting as a RANTES or MIP-1α antagonist. Such antagonists can be used in therapy to reduce inflammation. They are also useful in studying the properties of RANTES or of MIP-1α.

12 Claims, 11 Drawing Sheets

FIG. 1

```
27   ATGAAGGTCTCCGGGCACGCCCTCGCTGTCATCCTCATTGCTACTGCCCTCTGCGCTCCT    86
      M  K  V  S  A  A  R  L  A  V  I  L  I  A  T  A  L  C  A  P

87   GCATCTGCCTCCCCATATTCCTCGGACACCACACCCTGCTGTTTGCCTACATTGCCCGC   146
      A  S  A  S  P  Y  S  S  D  T  T  P  C  C  F  A  Y  I  A  R

147  CCACTGCCCCGTGCCACATCAAGGAGTATTTCTACACCAGTGGCAAGTGCTCCAACCCA   206
      P  L  P  R  A  H  I  K  E  Y  F  Y  T  S  G  K  C  S  N  P

207  GCAGTCGTCTTTGTCACCCGAAAGAACCGCCAAGTGTGCCAACCCAGAGAAGAAATGG   266
      A  V  V  F  V  T  R  K  N  R  Q  V  C  A  N  P  E  K  K  W

267  GTTCGGGAGTACATCAACTCTTTGGAGATGAGCTAGG   303
      V  R  E  Y  I  N  S  L  E  M  S  *
```

CC Chemokines induce chemotaxis in THP-1 cells.

|  | $EC_{50}$ (nM) |
|---|---|
| MCP-1 | 1 |
| MIP-1a | 0.2 |
| RANTES | 0.68 |

Inhibition of Chemokine induced Chemotaxis by Met-Rantes (GR 231774)

[Agonist] = 5 × $EC_{50}$

|  | $IC_{50}$ (nM) |
|---|---|
| ○ Mip-1α | 0.49 |
| ● RANTES | 8.18 |
| □ MCP-1 | ----- |

CC Chemokines induce Calcium flux in THP-1 cells.

|        | EC$_{50}$ (nM) |
|--------|----------------|
| Mip-1α | 4.6            |
| RANTES | 13.21          |

Inhibition of RANTES induced Calcium flux in THP-1 cells by Met-RANTES

RANTES at 5 x $EC_{50}$ concentration

Competition of $^{125}$I-RANTES binding to THP-1 cells by Met-RANTES (GR 231774)

$IC_{50}$ = 25 +/- 1.2 nM (n = 4 experiments)

[$^{125}$I]RANTES at 0.4 nM

Antagonism of RANTES induced chemotaxis by Leu-RANTES

Antagonism of RANTES induced chemotaxis of THP-1 cells by Glutamine-RANTES (Q-RANTES)

[Q-RANTES] (nM)

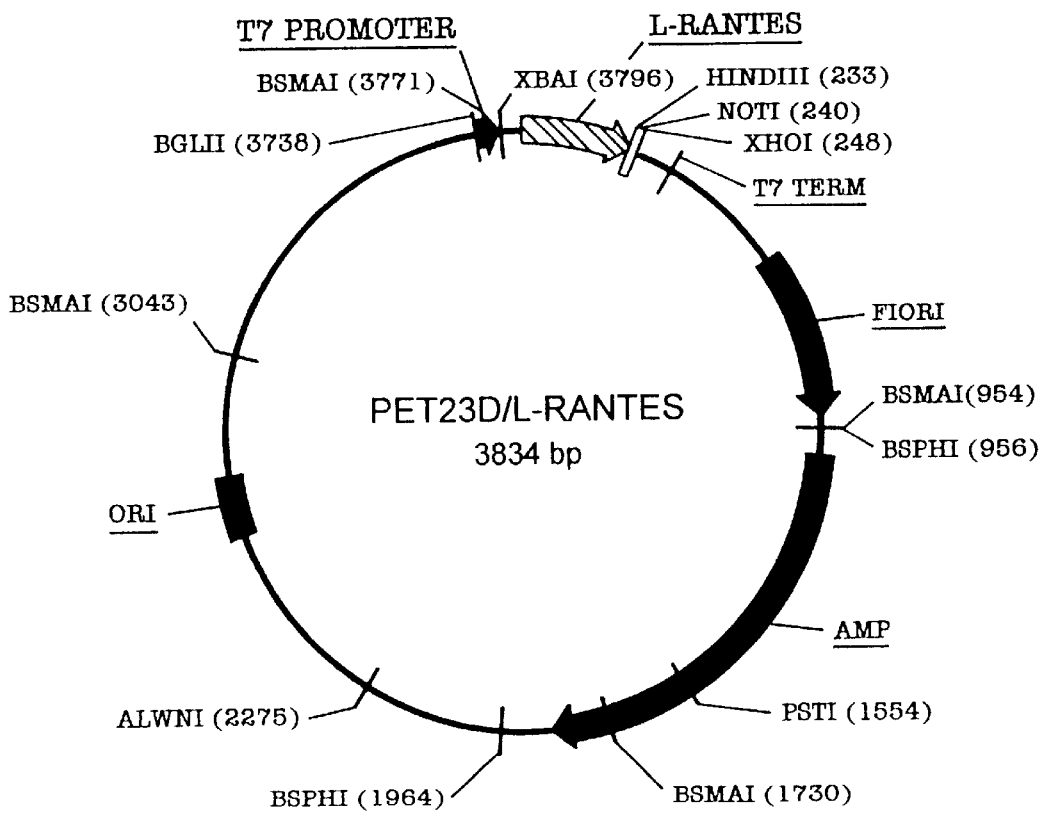

```
     +2   M   K   K   K   W   P   R   L   S   P   Y   S   S   D   T   T
     1   CATGAAAAAA AAATGGCCAA GGCTGTCCCC GTACTCCTCC GACACCACCC
         GTACTTTTTT TTTACCGGTT CCGACAGGGG CATGAGGAGG CTGTGGTGGG

+2   P   C   C   F   A   Y   I   A   R   P   L   P   R   A   H   I   K
    51   CGTGCTGCTT TGCCTACATT GCCCGCCCAC TGCCCCGTGC CCACATCAAG
         GCACGACGAA ACGGATGTAA CGGGCGGGTG ACGGGGCACG GGTGTAGTTC

+2   E   Y   F   Y   T   S   G   K   C   S   N   P   A   V   V   F   V
   101   GAGTATTTCT ACACCAGTGG CAAGTGCTCC AACCCAGCAG TCGTCTTTGT
         CTCATAAAGA TGTGGTCACC GTTCACGAGG TTGGGTCGTC AGCAGAAACA

+2   T   R   K   N   R   Q   V   C   A   N   P   E   K   K   W   V
   151   CACCCGAAAG AACCGCCAAG TGTGTGCCAA CCCAGAGAAG AAATGGGTTC
         GTGGGCTTTC TTGGCGGTTC ACACACGGTT GGGTCTCTTC TTTACCCAAG

+2   R   E   Y   I   N   S   L   E   M   S   *
                                                     HINDIII NOTI     XHOI
                                                     ───────────────  ────
   201   GGGAGTACAT CAACTCTTTG GAGATGAGCT AAAGCTTGCG GCCGCACTCG
         CCCTCATGTA GTTGAGAAAC CTCTACTCGA TTTCGAACGC CGGCGTGAGC
```

FIG. 11

METHOD OF TREATMENT WITH A RANTES ANTAGONIST POLYPEPTIDE

This application is a continuation of Ser. No. 08/836,922 (now U.S. Pat. No. 6,159,711), filed May 23, 1997 under 35 U.S.C. 371 from Int'l Appln. No. PCT/GB95/02861, filed Dec. 7, 1995 designating the United States and published in English.

The present invention relates to derivatives of RANTES and their uses.

The protein known as RANTES was originally cloned by Schall T. J. et al., (*J. Immunol.* 141 1018–1025 (1988)) in Krenskyp's laboratory at Stanford University School of Medicine. The term RANTES is derived from the phrase "Raised on activation, normal T-cell derived and secreted" (relevant letters underlined). Its expression is inducible by antigen stimulation or mutagen activation of T-cells. The protein is a member of the chemokine superfamily (Schall T. J., *Cytokine* 3 165–183 (1991); Oppenheim, J. J. et al., *Ann. Rev. Immunol.* 9 617–48 (1991)). The pure protein was first identified in 1992 in platelets (Kameyoshi et al., *J. Exp. Med.* 176 587–592 (1992)). It is a potent attractor for eosinophils, $CD4^+CD45RO^+$ T-cells, and also for monocytes. It has a sixty-eight amino acid sequence.

A receptor for RANTES has recently been cloned (Gao, J. L. et al., *J. Exp. Med.* 177 1421–7 (1993); Neote, K., et al., *Cell* 72 415–25 (1993))—and this has been shown to bind chemokines in the rank order of potency of MIP-1α>RANTES.

The present invention provides polypeptides which are antagonists of RANTES and/or of MIP-1α.

Despite the considerable interest in cytokines generally and the work discussed above on RANTES and RANTES receptors in particular, prior to the present invention there has been no disclosure of the above antagonists or of the possible utilities of such antagonists.

According to the present invention there is provided a polypeptide having substantial amino acid sequence homology with RANTES and functioning as an antagonist to RANTES and/or MIP-1α in respect of one or more of the following:

(a) the chemotaxis of THP-1 cells in response to RANTES and/or in response to MIP-1α;

(b) the mobilisation of calcium ions in THP-1 cells due to the presence of RANTES and/or due to the presence of MIP-1α; and (c) the binding of RANTES and/or of MIP-1α to receptors of THP-1 cells.

The polypeptides provided by the present invention are useful in further characterising RANTES and its effects—for example in studying RANTES induced chemotaxis, mobilisation of calcium ions and receptor binding. They are also useful in the characterisation of the binding of RANTES to its receptors. They are useful in studying MIP-1α for corresponding reasons.

Additionally, the polypeptides of the present invention are believed to be useful in the treatment of various diseases, as will be discussed later.

A preferred polypeptide of the present invention acts as an antagonist to RANTES and/or to MIP-1α due to the presence of one or more N-terminal amino acids (which are not present at the corresponding position in RANTES and which can therefore be regarded as additional N-terminal amino acids relative to those present at the N-terminus of RANTES). These N-terminal amino acids are preferably naturally occurring (L-) amino acids (which can be incorporated by using recombinant DNA techniques or by peptide fusion techniques). However non-naturally occurring amino acids (e.g. D-amino acids) may be used. These may be incorporated by using chemical synthesis techniques.

There may be only one such additional amino acid, in which case it may be Leucine or Methionine, for example. Such polypeptides can be prepared by any suitable techniques (e.g. by using gene cloning techniques, chemical synthesis, etc.). In one embodiment of the present invention they are prepared by providing a larger polypeptide comprising a desired sequence and then using enzymatic cleavage to produce a polypeptide consisting of the desired sequence.

The polypeptides of the present invention may comprise more than one additional N-terminal amino acids e.g. they may include up to five, up to ten or up to twenty additional amino acids. In some cases over twenty additional N-terminal amino acids may be present.

Again, any suitable techniques can be used to prepare such polypeptides.

The various aspects of the present invention will now be discussed in further detail below.

The present inventors have discovered that using an *E. coli* expression system intended to express RANTES in a form corresponding to mature human RANTES (i.e. with the signal sequence removed) a polypeptide was expressed in which an additional N-terminal methionine was present (this was not cleaved from the remaining sequence by endogenous *E. coli* proteases). It was surprisingly found that the presence of this additional amino acid substantially changed the characteristics of the polypeptide relative to those of RANTES. The methionylated polypeptide (referred to herein as methionylated RANTES or Met-RANTES) was found to act as an antagonist of RANTES and of MIP-1α in various assays and was not found to have any substantial agonist activity.

It should be appreciated that in many cases where N-terminal methionylation occurs in *E. coli*, it makes little or no difference to a polypeptide's properties or results in it merely having reduced levels of its previous biological activity. It was therefore totally unexpected that N-terminal methionylation would in the case of the present invention actually result in antagonistic activity.

In order to determine whether or not this effect was limited to the present of an N-terminal methionine, another polypeptide was produced, in which the N-terminal methionine was replaced with an N-terminal Leucine. Again, this was found to act as an antagonist of RANTES, as was a further polypeptide in which the N-terminal methionine was replaced with an N-terminal Glutamine.

In a preferred form, the polypeptide of the present invention has the sequence:

(i) MSPYSSDT TPCCFAYIAR PLPRAHIKEY FYTS-GKCSNP AVVFVTRKNR QVCANPEKKW VREY-INSLEM S (sometimes referred to herein as "Met-RANTES")

(ii) LSPYSSDT TPCCFAYIAR PLPRAHIKEY FYTS-GKCSNP AVVFVTRKNR QVCANPEKKW VREY-INSLEM S (sometimes referred to herein as "Leu-RANTES")

or (iii) QSPYSSDT TPCCFAYIAR PLPRAHIKEY FYTS-GKCSNP AVVFVTRKNR QVCANPEKKW VREY-INSLEM S (sometimes referred to herein as "Gln-RANTES")

or has a sequence which is substantially homologous with any of the above sequences. The polypeptide may be in a glycosylated or unglycosylated form.

The term "substantially homologous" when used herein includes amino acid sequences having at least 40%, 50%, 60%, 70%, 80%, 90%, 95% or 99% sequence homology with the given sequence (in order of preference). This term can include, but is not limited to, amino acid sequences having from 1 to 20, from 1 to 10 or from 1 to 5 single amino acid deletions, insertions or substitutions relative to a given sequence—provided that the resultant polypeptide acts as an antagonist to RANTES or to MIP-1α.

The polypeptide may be in substantially pure form. It may be isolated from naturally occurring polypeptides.

It should be noted that it is well known in the art that certain amino acids can be replaced with others resulting in no substantial change in the properties of a polypeptide. Such possibilities are within the scope of the present invention.

It should also be noted that deletions or insertions of amino acids can often be made which do not substantially change the properties of a polypeptide. The present invention includes such deletions or insertions (which may be, for example up to 10, 20 or 50% of the length of the specific antagonists sequence given above). The present invention also includes within its scope fusion proteins in which the polypeptides of the present invention are fused to another moiety. This may be done, for example, for the purpose of labelling or for a medicinal purpose.

The present inventors have demonstrated that a polypeptide of the present invention can act as an antagonist to the effects of RANTES or of MIP-1α in chemotaxis, calcium mobilisation and receptor binding in THP-1 cells (a monocytic cell line). These cells are available from ATCC (American Tissue Culture Collection) and act as a good model system for studying RANTES because they show calcium responses and chemotactic responses to RANTES and MIP-1α, as well as other chemokines such as MCP-1. The polypeptide can also act as an antagonist of RANTES or of MIP-1α in chemotaxis, calcium mobilisation and receptor binding in these cells. MIP-1α was originally identified as part of a Macrophage Inflammatory Polypeptide fraction (which was split into MIP-1α and -β) (Obaru, K et al., J Biochem 99:885–894 (1988). Sippel, P F et al., J Immunol 142:1582–1590 (1989)). It shows chemotactic activity towards T-cells and monocytes. It has also been shown to be a potent inhibitor of stem cell proliferation.

Based upon these observations it is believed that the polypeptides of the present invention can be of utility in blocking the effects of RANTES and/or MIP-1α and can therefore be of use in therapy. A preferred use of the polypeptides of the present invention is in blocking the effects of RANTES and/or MIP-1α in the recruitment and/or activation of pro-inflammatory cells. The present invention may therefore be of utility in the treatment of diseases such as asthma, allergic rhinitis, atopic dermatitis, atheroma/atheroschleosis and rheumatoid arthritis.

In addition to the polypeptides discussed above, the present invention also covers DNA sequences coding for such polypeptides (which may be in isolated or recombinant form), vectors incorporating such sequences and host cells incorporating such vectors which are capable of expressing the polypeptides of the present invention.

The polypeptides of the present invention can be produced by expression from prokaryotic or eukaryotic host cells, utilising an appropriate DNA coding sequence. Appropriate techniques are disclosed in Sambrook et al., (1989) Molecular Cloning: A Laboratory Manual, Cold Spring Harbor, Laboratory Press, USA. Alternatively, they may be produced by covalently modifying RANTES. This can be done, for example, by methionylating RANTES as its N-terminus.

BRIEF DESCRIPTION OF THE DRAWINGS

The present invention will now be described by way of example only, with reference to the accompanying drawing, wherein:

FIG. 1 shows a nucleotide sequence of a RANTES coding sequence which was cloned in E. coli, together with the amino acid sequence coded for by this nucleotide sequence.

FIG. 11 shows a map of plasmid pET23d/L-RANTES.

Figure 2:
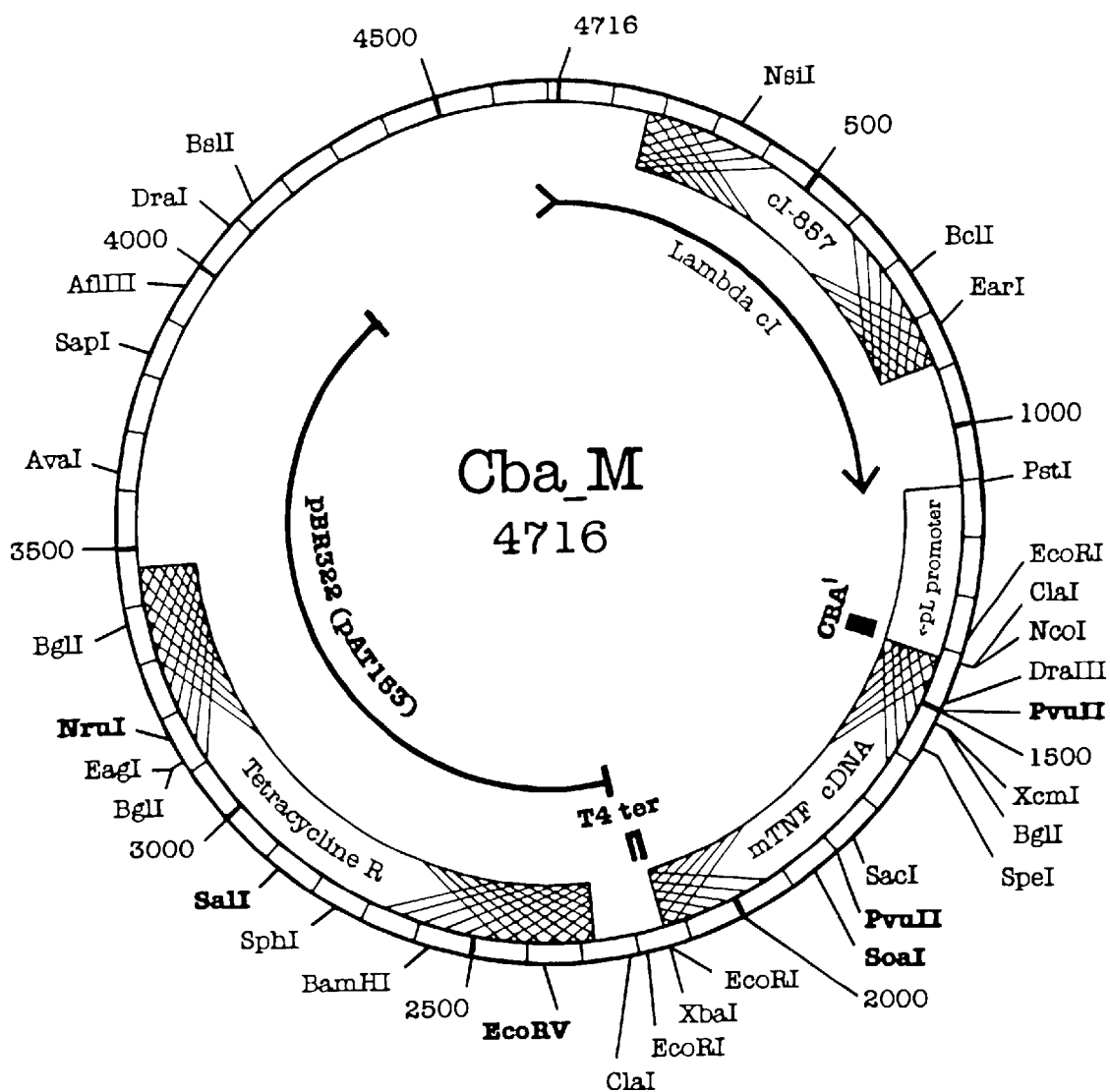
FIG. 2 shows a map of plasmid pCBA-M.

EXAMPLE (a) Cloning of Human RANTES coding sequence by PCR

Human RANTES was cloned from a human bone marrow λGT11 cDNA library (Clontech) by PCR. Briefly, total cDNA inserts in the bone marrow library were first amplified using λGT11 primers which flanked the EcoRI cloning site in a 100 μl reaction containing 2 μl of phage stock ($10^6$ pfus), 10 mM Tris-HCl pH 8.3, 50 mM KCl, 1.5 mM $MgCl_2$, 0.2 mM dNTPs, 2.5 units AMPLITAQ™ (Perkin Elmer-Cetus) and 1 μM of each primer (λGT11PCR-1 (forward primer) 5' GATTGGTGGCGACGACTCCT and λGT11PCR-2 (reverse primer) 5' CAACTGGTAATGGTAGCGAC) for 30 cycles of 95° C. 2 min, 55° C. 2 min and 72° C. 5 min in a Techne PHC-2 thermal cycler. One tenth of the reaction mixture was then subjected to a 2nd round of PCR in a 100 μl reaction now containing 1 μM each of specific primers (RANTES-1 5' CCATGAAGGTCTCCGCGGCAC sense and RANTES-2 5' CCTAGCTCATCTCCAAAGAG antisense) based on the published RANTES sequence (Schall T. J. et al., (J. Immunol. 141 1018–1025 (1988)) for 30 cycles of 95° C. 2 min, 55° C. 2 min and 72° C. 2 min. PCR products were visualised on 3% Nu-Sieve (FMC) agarose gels stained with 0.5 μg/ml ethidium bromide and bands migrating at the predicted size of RANTES cDNA (278 bp) were gel purified by standard methods (Sambrook J. et al., (1989) Molecular Cloning—A Laboratory Manual, Cold Spring Harbor, Laboratory Press, USA). Gel purified DNA was then rendered blunt-ended by sequential treatment with T4 polynucleotide kinase (New England Biolabs) according to the manufacturers' instructions, in a total volume of 50 μl for 1 h at 37° C. After this time, 2.5 μl of 2.5 mM dNTPs and 1 μl of E. coli DNA polymerase I Klenow fragment (New England Biolabs) were added and the incubation continued for a further 30 min at 37° C. The reaction mixture was then heat inactivated at 70° C. for 30 min and then extracted once with Tris-HCl pH 8.0 saturated phenol/chloroform (1:1 v/v). DNA was precipitated by addition of 10 μl 3M sodium acetate pH 5.5, 1 μl glycogen (20 mg/ml) (Boehringer) and 250 μl ethanol at −20° C. The DNA was recovered by centrifugation at 10,000×g for 20 min at 4° C. and washed with 70% ethanol. The final pellet was resuspended in sterile water at a concentration of 10 ng/µl.

Blunt-ended PCR product (10 ng) was ligated to 50 ng of EcoRV digested, alkaline phosphatase treated pBluescript II SK-plasmid (Stratagene) in a 20 µl volume using 2 µl of T4 DNA ligase (400,000 units/ml) (New England Biolabs) for at least 16 h at 15° C. Ligation products were diluted to 100 µl with 1×TE (10 mM Tris-HCl pH 8.0/1 mM EDTA) and phenol/chloroform extracted as described previously. Ligation products were precipitated by the addition of 10 µl 3M sodium acetate pH 5.5, 1 µl glycogen (20 mg/ml) and 250 µl ethanol for 15 min at −70° C. DNA was recovered by centrifugation as described above and resuspended in 10 µl of sterile water. 5 µl of resuspended ligation products were then electroporated into electrocompetent *E. coli* strain XL-1 blue (40 µl) using a Bio Rad Gene pulser according to the manufacturers' instructions. Following electroporation, 1 ml of LB medium was added and cells were grown at 37° C. for 1 h. After this time, 100 µl aliquots of the culture medium were plated on LB plates containing 100 µg/ml of ampicillin and grown up for 16 h at 37° C. Individual bacterial colonies were then picked into 5 ml of LB medium containing 100 µg/ml of ampicillin and grown overnight at 37° C. Small scale plasmid DNA preparations (mini-preps) were then made from 3 ml of each culture using a WIZARD™ mini-prep DNA purification system (Promega) according to the manufacturers' instructions. 3 µl aliquots of mini-prep DNA was then digested with restriction enzymes HindIII and EcoRI (both from New England Biolabs) according to the manufacturers' instructions in a reaction volume of 15 µl. Reaction products were analysed on 1% agarose gels containing 0.5 µg/ml ethidium bromide. Miniprep DNAs which yielded an insert size of approximately 280 bp were then subjected to DNA sequence analysis using T3 and T7 primers and Sequenase (USB) according to the manufacturers' instructions.

The pBluescript II SK-cloning vector was prepared as follows: 20 µg of CsCl gradient purified plasmid was digested in a reaction volume of 100 µl of 2 h at 37° C. with 200 units of EcoRV (New England Biolabs) according to the manufacturers' instructions. After 2 h, the digested vector was treated with 10 µl of calf intestinal alkaline phosphatase (20 units/ml) (Boehringer) for a further 30 min at 37° C. The reaction mixture was inactivated by heating at 68° C. for 15 min and then extracted once with Tris-HCl pH 8.0 saturated phenol/chloroform (1:1 v/v). Plasmid DNA was precipitated by addition of 10 µl 3M sodium acetate pH 5.5 and 250 µl ethanol at −20° C. The DNA was recovered by centrifugation at 10,000×g for 20 min at 4° C., washed with 70% ethanol. The final pellet was resuspended in sterile water at a concentration of 50 ng/ml.

Sequencing revealed that all clones obtained were identical to the published sequence except for a single base change at nucleotide 22 in the PCR sequence which would result in an Arg to Pro change in the proposed signal sequence of the RANTES propeptide.

This is illustrated in FIG. 1, where the DNA coding sequence cloned is given, together with the corresponding amino acid sequence.

(b) Preparation of an expression vector for methionylated RANTES (a RANTES antagonist)

The construct containing the gene for RANTES was PCR'd using the primers

5'TTAATTAATTAA<u>ATCGATT</u>
<u>CATATG</u>.TCC.CCA.TAT.TCC.TCG.GAC.AC-3' where the two underlined sections are a Cla1 and an Nde1 restriction site, respectively (the Nde1 site including part of an initiation methionine codon) and

5'-TACTGATATAAATCTAGACTAGCT-
CATCTCCAAAGAGTTG-3'

This fragment was then cleaved with Cla1 at the 5' end and Xba1 at the 3' end. The plasmid pCba-M, which is shown in FIG. 2, was then cleaved with Xba1/Sal1. The large fragment was the cleaved with Sal1 and Cla1. Then a three-way ligation was carried out using the small Sal1/Xba1 fragment from the first digest, the Sal1/Cla1 fragment from the second digest, and the PCR fragment, to produce a construct similar to pCba-M where the mTNF gene was replaced by that for the secreted form of human RANTES starting with an initiating methionine. (The secreted form of human RANTES does not include the first twenty three amino acids of the amino acid sequence shown in FIG. 1. It includes the remaining amino acids shown in FIG. 1 and begins with the amino acids SPY . . . ).

Figure 3:
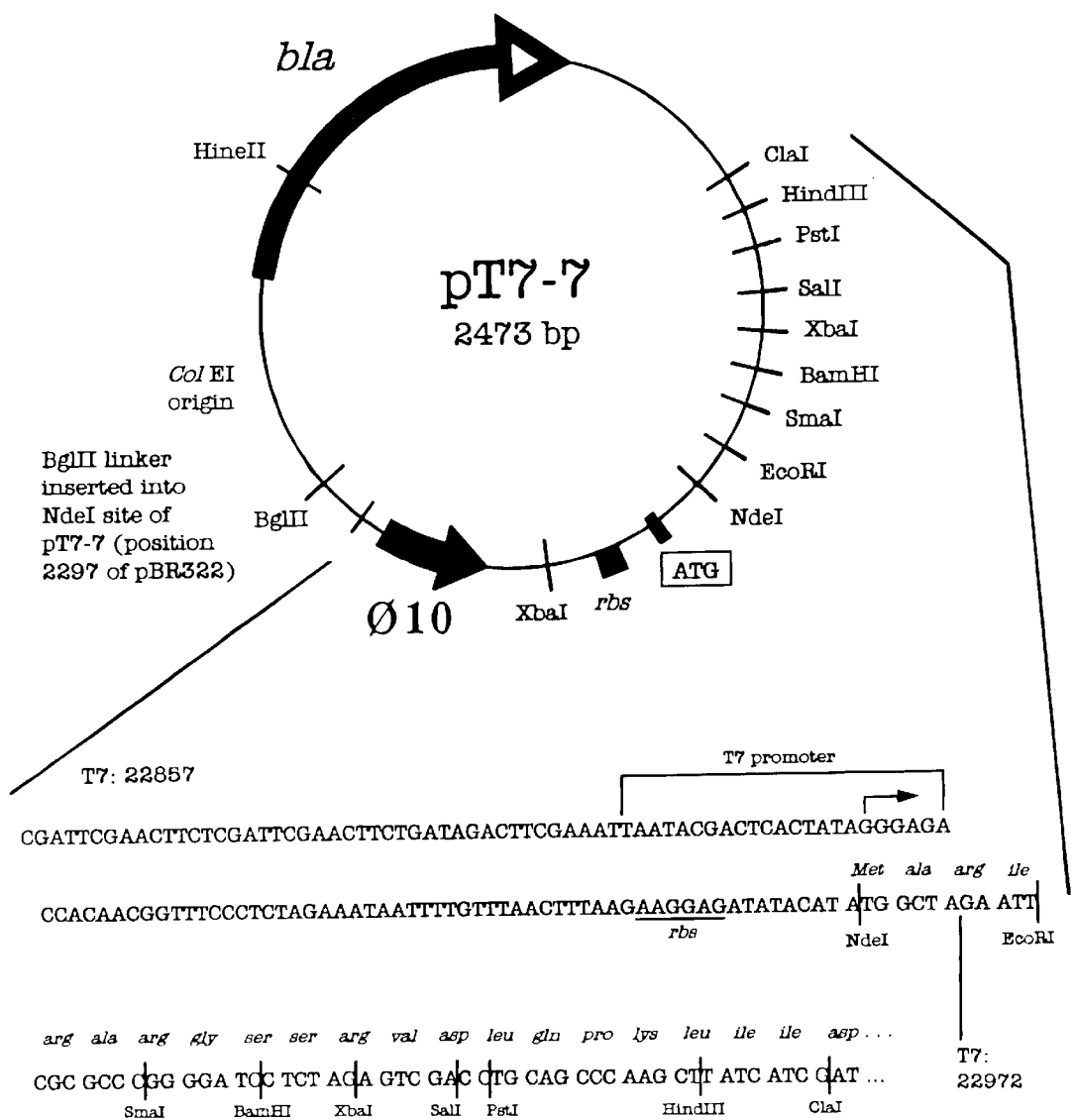
FIG. 3 shows a map of plasmid pT7-7.

This Nde1/Sal1 fragment was then removed from this vector and put into the t7 expression plasmid pT7-7, which is shown in FIG. 3. This fragment contains the gene of interest plus 600 bp of other material, but later experiments (not included herein) showed that the removal of the other material (vector sequences) had no effect on the expression levels.

The pT7 type expression vector is discussed by Studier F W, Roseberg A H et al., in Meth Enzymol, 185, 60–89, (1990). The construct was then transformed into *E. coli* BL21 (DE3) strain (F-ompT, hsd $s_B$ ($r_B^-$, $m_B^-$) containing the LysS gene on plasmid pACYC184 (Chang and Cohen, J. Bact, 134, 1141, 1978). The expression vector requires the T7 polymerase to be induced in order for protein expression to take place. The T7 polymerase is induced in the cells by the addition of IPTG (isopropylthiogalactoside) to the medium.

(c) Demonstration that Met-RANTES does indeed show Antagonistic Activities (i) Chemotaxis assay In vitro chemotaxis was carried out using 96 well chambers (Neuro Probe MB series, Cabin John, Md. 20818, USA) according to the manufacturers instructions. Chemotaxis induced by the CC chemokines, RANTES, λGT11 and MCP-1 was assayed using the human monocytic cell-line, THP-1. 4×10$^5$ THP-1 cells in 200 µl RPMI 1640 medium (Gibco) containing 2% inactivated fetal calf serum were incubated in each well of the upper chamber. 370 µl of RPMI 1640 medium (without FCS) containing the chemoattractant (i.e. the chemokine) in appropriate dilutions was placed in the lower chamber. For the inhibition of chemotaxis, the chemoattractant was kept at a constant concentration of 5× the EC$_{50}$, determined previously for each chemoidne, and Met-RANTES was added at varying concentrations. The chambers were incubated for 1 h at 37° C. under 5% CO$_2$. The medium was removed from the upper chamber and replaced with PBS containing 20 mM EDTA, and the chambers incubated for 30 min at 4° C. The PBS was removed from the upper walls which were then wiped dry. The unit was centrifuged for 10 min at 1800 rpm to harvest the cells in the bottom chamber, and the supernatant removed by aspiration. The cells in the bottom chambers were measured using the Cell titer 98™ Non-Radioactive Cell Proliferation Assay (Fromega, Madison, USA) which monitors the conversion of terazolium blue into its formazan product. 100 µl of a 10% solution of the Dye in RPMI 1640 medium was added to each well, and the chamber incubated overnight at 37° C. under 5% $CO_2$. 100 μl of Solubilisation solution was then added to each well, and the absorbance need at 590 nm after 4 h in a Thermomax microtitre plate reader (Molecular Devices, Palo Alto, Calif.).

Figure 4:
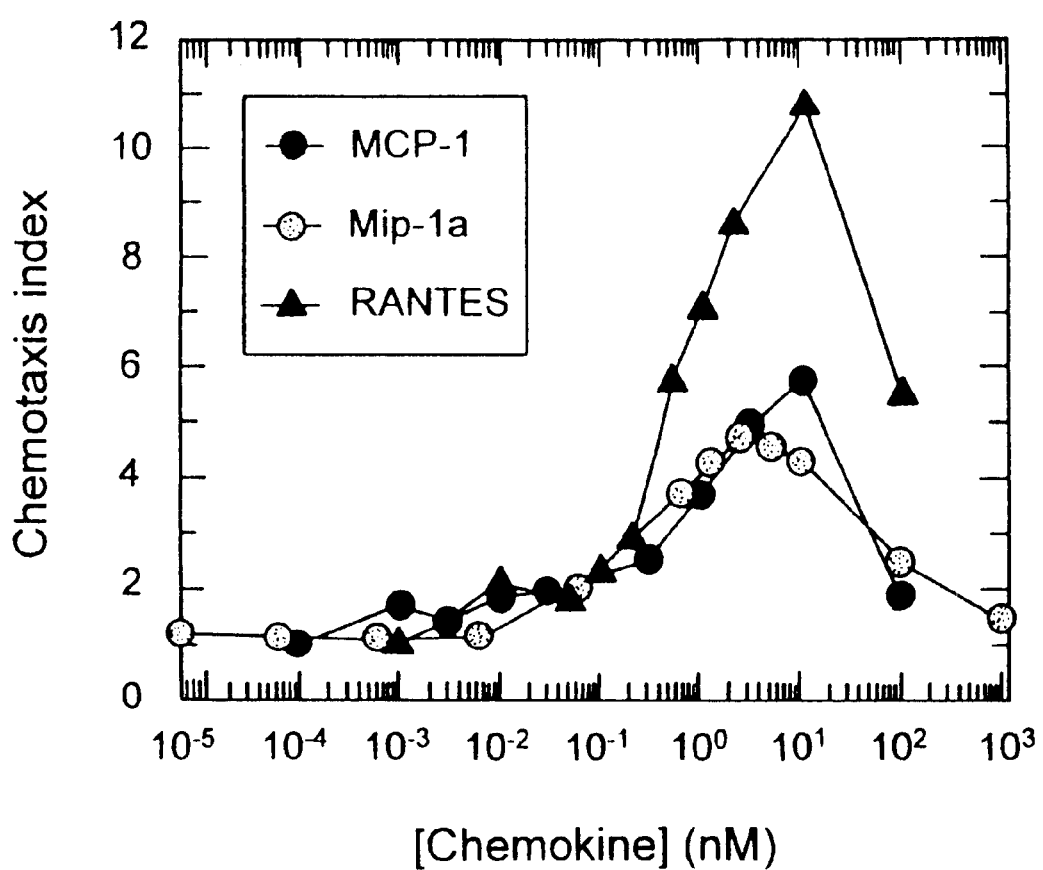
FIG. 4 shows that various chemokines can induce chemotaxis in THP-1 cells.
Figure 5:
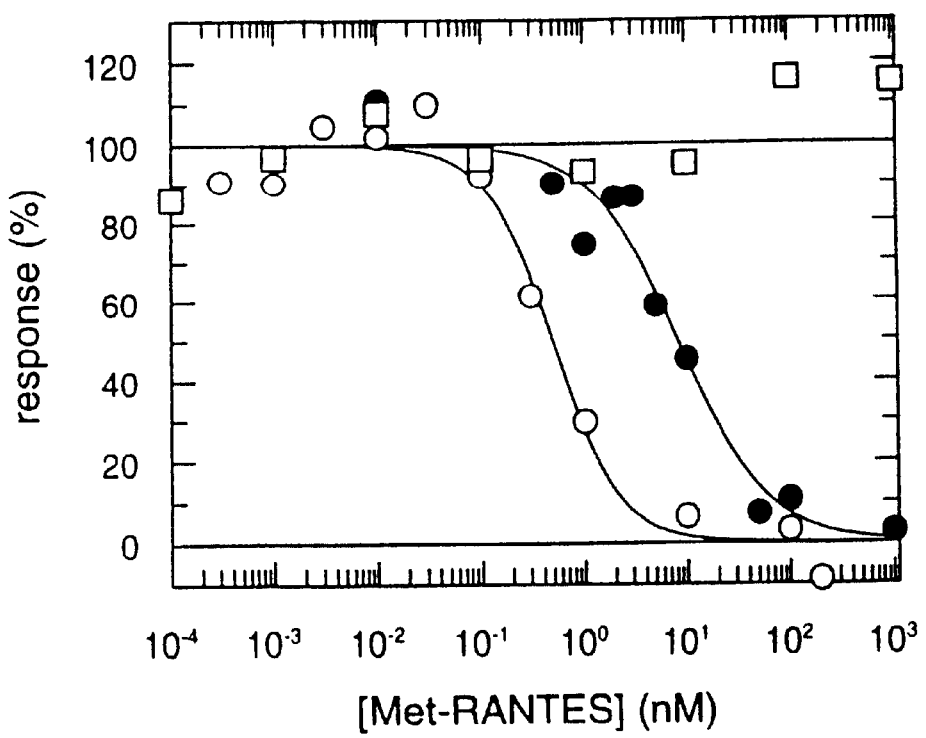
FIG. 5 shows that Met-RANTES can inhibit MIP-1α and RANTES induced chemotaxis in THP-1 cells.

The results are shown in FIG. 4 and FIG. 5.

(ii) Calcium Flux

The calcium flux induced by the chemokines RANTES and MIP-1α was measured according to Tsien R Y., Pozzan T., and Rink T J., ((1982) "Calcium homeostasis in intact lymphocytes: cytoplasmic free calcium monitored with a new, intracellularly trapped fluorescent indicator", *J Cell Biology* 94) but using Fura-2/AM (Fluka) instead of Quin2 as the fluorescent indicator. THP-1 cells were harvested at less than $10^6$/ml to ensure that they were in the exponential phase. The cells were resuspended in Krebs-Ringer solution containing 0.2% product was cloned into the T7 based *E. coli* expression vector pET23d (Novagen) using a SacI site introduced at the 5' end of the gene and a BsmAI site designed to yield a HindIII compatiable overhang at the 3' end of the gene. Genes encoding N-terminal variants of human RANTES were then created by inserting oligonucleotides encoding the varients immediately 5' to the RANTES coding sequence. For this purpose, the truncated RANTES clone in pET23d was digested with SacI, followed by T4 DNA polymerase to remove the protruding 3" overhang left by SacI and then a second digestion with NcoI. Oligonucleotides encoding the peptide sequence MKKKWPRLSPYSSDTTP were then cloned into the digested vector. Expression of the pET23d/L-RANTES construct was carried out as described for the pT7-7 construct.

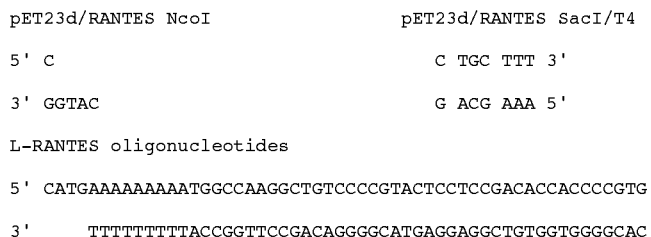

Figure 6:
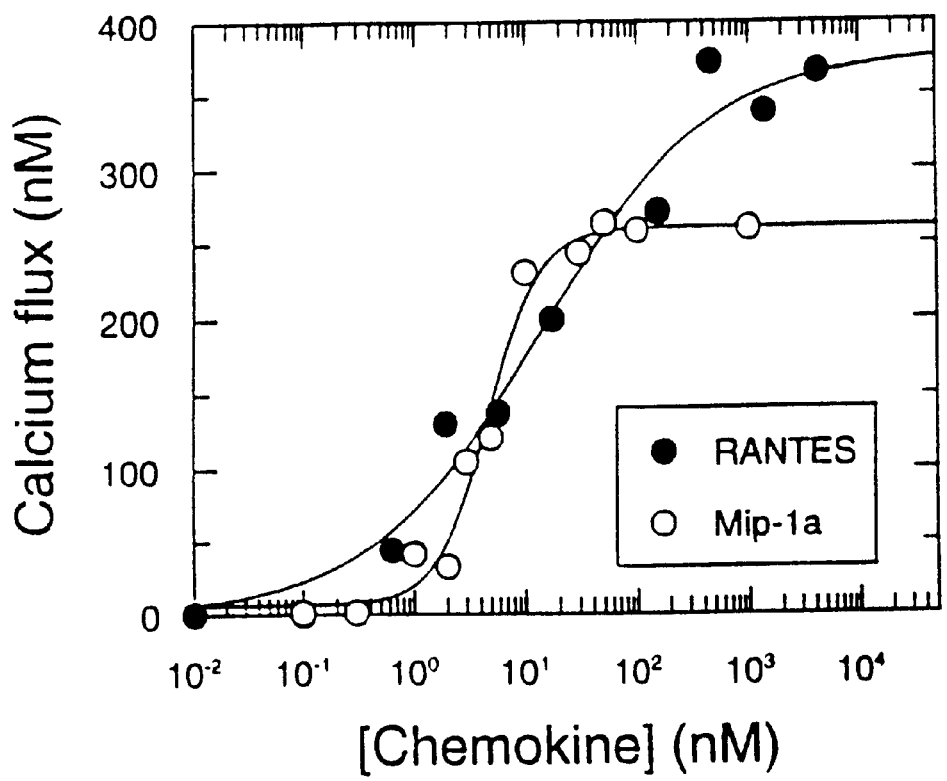
FIG. 6 shows that various chemokines can induce calcium flux in THP-1 cells.
Figure 7:
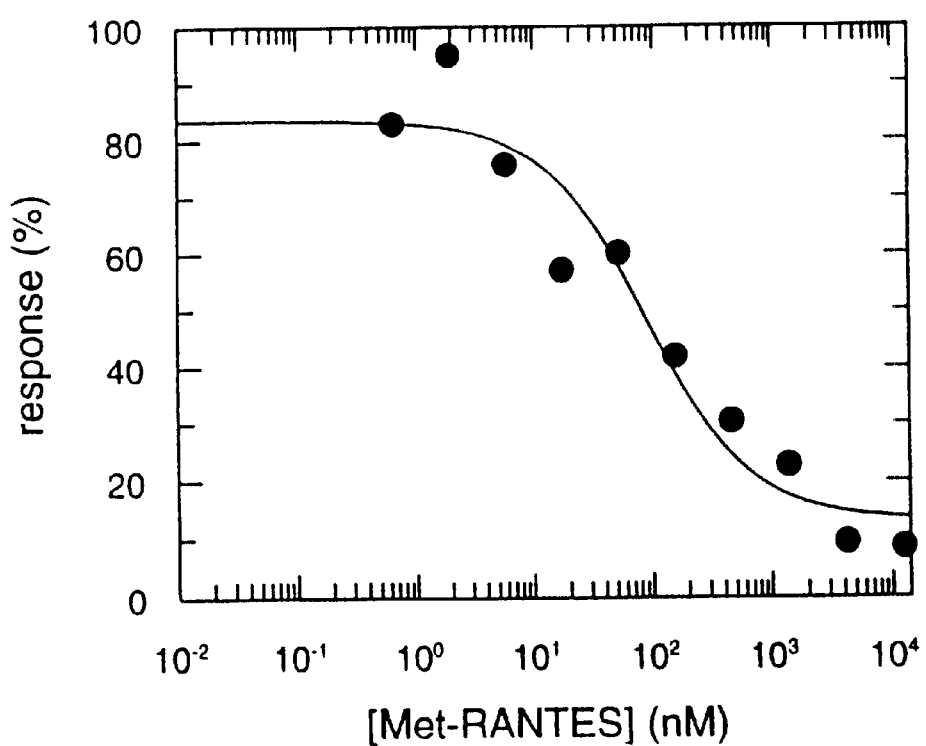
FIG. 7 shows that Met-RANTES can inhibit a RANTES induced calcium response in THP-1 cells.

Fura-2/AM and 1 mg/ml BSA, at a concentration of $10^6$/ml, and incubated at 37° C. for 30 min in the absence of light. The cells were harvested by centrifugation and resuspended in Krebs-Ringer solution and kept on ice. 1 ml aliquots were incubated at 37° C. for 2 min prior to use. The chemokines were added to the cell suspension under stirring. To study the inhibition by Met-RANTES, aliquots of the antagonist were added to the cells during the 2 min incubation at 37° C. at varying concentrations. The results are shown in FIG. 6 and FIG. 7.

(iii) Receptor Binding Assay

Figure 8:
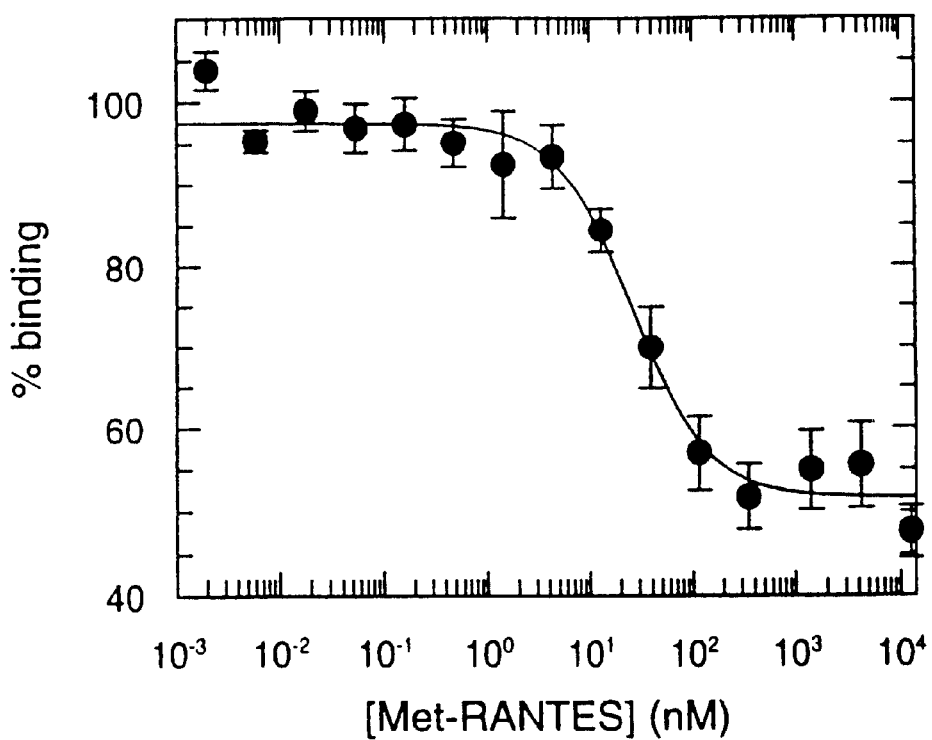
FIG. 8 shows competitive binding of Met-RANTES with RANTES to CCKR1 receptors.

The competition assay was carried out in 96 well multi-screen filter-phase (Millipore, MADV N6500) which had been pretreated for 2 h with 50 mM HEPES buffer, pH 7.2 containing 1 mM $CaCl_2$, 5 mM $MgCl_2$, and 0.5% BSA, (binding buffer). The assay was performed using either THP-1 cells or COS cells expressing the recombinant CC-CKR1 receptor (Neote, K., DiGregorio, Mak, J. Y., Horuk, R., and Schall, T. J., (1993) Molecular cloning, functional expression, and signalling characteristics of a C—C chemokine receptor, *Cell* 72 415–425; Gao, J. L., et al, *J. Exp. Med.* 177 1421–7 (1993)). Each well contained $10^5$ cells in a volume of 150 μl of binding buffer containing 0.4 nM [$I^{125}$]Mip-1a or 0.4 nM [$I^{125}$]RANTES (new England Nuclear, Nex 277) and varying concentrations of competing Met-RANTES. Assays were performed in triplicate. After 90 min incubation at 4° C., the cells were washed 4 times with 200 μl ice cold binding buffer containing 0.5 M NaCl which was removed by aspiration. The filters were dried, 3.5 ml Ultima Gold Scintillation fluid added (Packard) and counted on a Beckman LS5000 counter. The results are shown in FIG. 8.

(d) Preparation of Leu-RANTES (also referred to here as L-RANTES) and demonstration of antagonism The L-RANTES expression vector was made in two steps. First PCR was used to truncate the gene for human RANTES within the first cysteine codon and introduce unique restriction sites at either end of the gene. This PCR The pET23d/L-RANTES construct is one of a series of expression vectors, which can be used to generate RANTES with different amino acids at the −1 position. These T7 expression vectors encode proteins with N-terminal sequences of MKKKWPR-X-RANTES. X may be either L, I, Q, E or G for example. Cleavage with endo-Arg-C will yield different X-RANTES proteins.

Purification of Leu-RANTES was carried out as follows:

4 g *E. coli* cell paste were suspended in 15 ml 50 mM Tris-HCl buffer, pH 7.6, containing 1 mM dithiothreitol, 5 mM benzamidine-HCl, 0.1 mM phenylmethylsulfonyl fluoride and DNase (0.02 mg/ml) Cells were broken by three passages through a French Pressure cell, with 1 min sonication on ice after each passage. The resulting solution was centrifuged for 60 min at 10 000×g. The pellets were dissolved in 2 ml 100 mM Tris-HCl buffer, pH 8.0, containing 6 M Guanidine-HCl and 1 mM dithiothreitol. The solution was heated for 60 min at 60° C. to ensure monomerisation, cooled to room temperature and gel-filtered on a Superdex-200 16/60 column equilibrated in the same buffer. The fractions containing the recombinant RANTES construct (18 ml) were renatured by dropwise addition to 384 ml 100 mM Tris-HCl buffer, pH 8.0, containing 1 mM oxidised glutathione and 0.1 mM reduced glutathione, and stirred overnight. This solution was dialysed against 50 mM sodium acetate buffer, pH 4.5, and then applied to a HiLoad SP26/10 column equilibrated in the same buffer. The proteins were eluted by a linear gradient of 0–2 M NaCl in the same buffer. The fractions containing the renatured protein were dialysed against 3×5 liter 1% acetic acid and lyophilised.

To remove the KKKWPR hexapeptide from the fusion protein, the lyophilised powder was dissolved in water, and adjusted to 1 mg/ml 50 mM Tris-HCl buffer pH 8.0, To 2 mls of this solution, 20 μg Endoproteinase Arg C (Boehringer Mannheim) was added and the solution incubated for 2 h at 37° C. The digested protein was separated from the starting mateial by reverse-phase HPLC using a Nucleosil-$C_8$ (10×

250 mm) column equilibrated in 0.1% trifluoroacetic acid. The proteins were eluted with a gradient of 22.5–45% acetonitrile in 0.1% trifluoroacetic acid, lyophilised and stored at −80° C.

The antagonist activities on RANTES induced chemotaxis of THP-1 cells was tested as described for the Met-RANTES protein.

Figure 9:
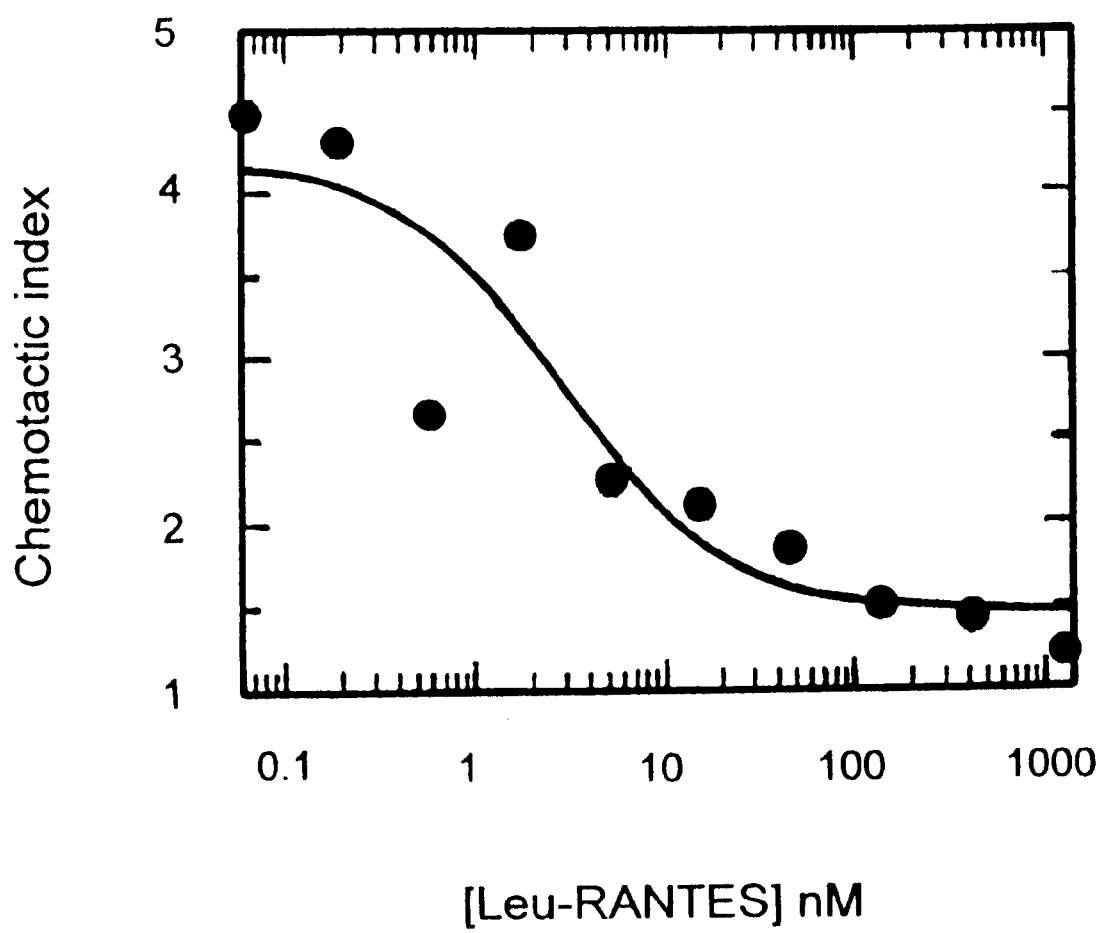
FIG. 9 shows that Leu-RANTES can act as an antagonist to RANTES-induced chemotaxis.

The results are shown in FIG. 9.

(e) Preparation of Gln-RANTES (sometimes referred to as Q-RANTES) and demonstration of antagonism The procedure described in (d) above was repeated mutatis mutandis in order to prepare Gln-RANTES.

Figure 10:
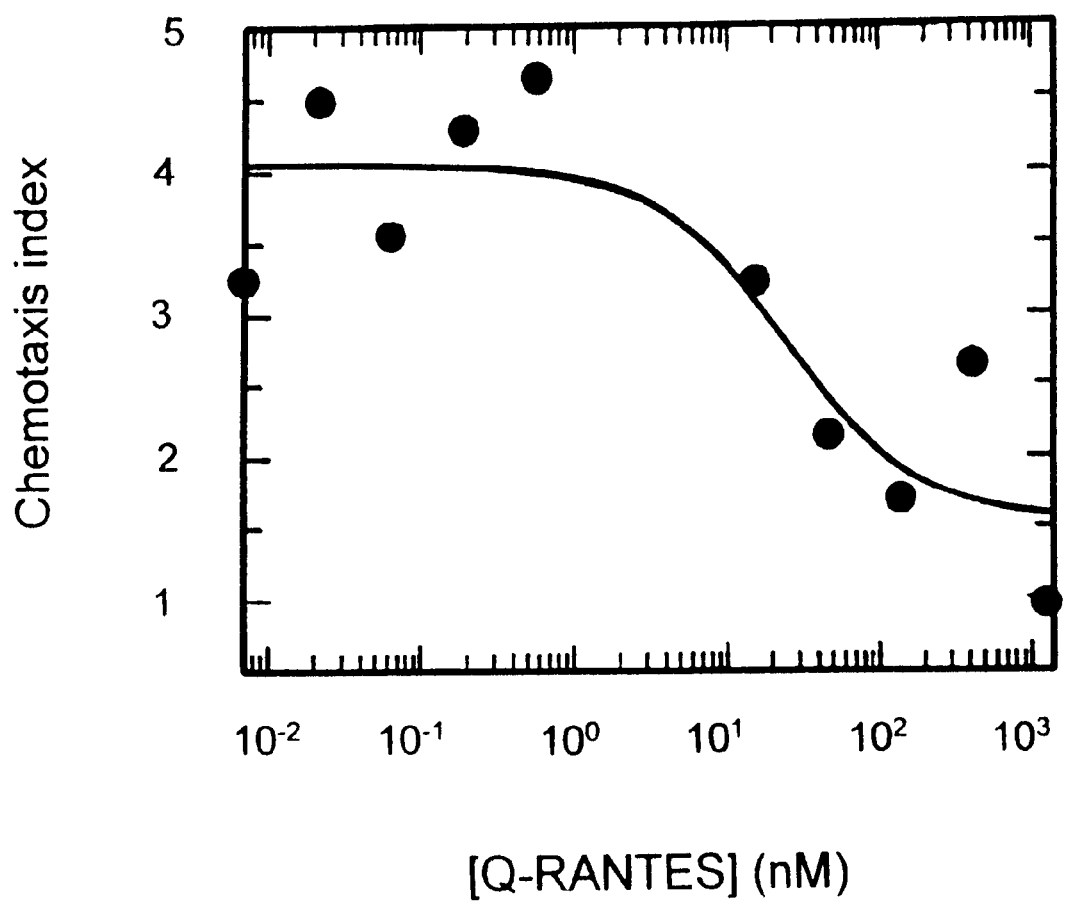
FIG. 10 shows that Gln-RANTES can act as an antagonist to RANTES-induced chemotaxis.

The antagonist activities of Gln-RANTES on RANTES induced chemotaxis of THP-1 cells was tested as described for the Met-RANTES protein. The results are shown in FIG. 10.

What is claimed is:

1. A method of inhibiting or reducing inflammation mediated by RANTES and/or MIP-1α comprising administering a polypeptide consisting of the sequence shown in SEQ ID NO:2, SEQ ID NO:3 or SEQ ID NO:4 to a patient.

2. A method according to claim 1 wherein the polypeptide consists of the sequence shown in SEQ ID NO:2.

3. A method according to claim 1 wherein the polypeptide consists of the sequence shown in SEQ ID NO:3.

4. A method according to claim 1 wherein the polypeptide consists of the sequence shown in SEQ ID NO:4.

5. A method of antagonizing the effects of RANTES and/or MIP-1α comprising administering a polypeptide consisting of the sequence shown in SEQ ID NO:2, SEQ ID NO:3 or SEQ ID NO:4 to a patient.

6. A method according to claim 5 wherein the polypeptide consists of the sequence shown in SEQ ID NO:2.

7. A method according to claim 5 wherein the polypeptide consists of the sequence shown in SEQ ID NO:3.

8. A method according to claim 5 wherein the polypeptide consists of the sequence shown in SEQ ID NO:4.

9. A method of inhibiting or reducing inflammation associated with rheumatoid arthritis or atherosclerosis comprising administering a polypeptide consisting of the sequence shown in SEQ ID NO:2, SEQ ID NO:3 or SEQ ID NO:4 to a patient.

10. A method according to claim 9 wherein the polypeptide consists of the sequence shown in SEQ ID NO:2.

11. A method according to claim 9 wherein the polypeptide consists of the sequence shown in SEQ ID NO:3.

12. A method according to claim 9 wherein the polypeptide consists of the sequence shown in SEQ ID NO:4.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Met Ser
65
```

(2) INFORMATION FOR SEQ ID NO: 2:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Ser Pro Tyr Ser Ser Asp Thr Thr Pro Cys Cys Phe Ala Tyr Ile
1               5                   10                  15

Ala Arg Pro Leu Pro Arg Ala His Ile Lys Glu Tyr Phe Tyr Thr Ser
                20                  25                  30

Gly Lys Cys Ser Asn Pro Ala Val Val Phe Val Thr Arg Lys Asn Arg
            35                  40                  45

Gln Val Cys Ala Asn Pro Glu Lys Lys Trp Val Arg Glu Tyr Ile Asn
        50                  55                  60

Ser Leu Glu Met Ser
65
```

(2) INFORMATION FOR SEQ ID NO: 3:

(i) SEQUENCE CHARACTERISTICS:
        (A) LENGTH: 69 amino acids (B) TYPE: amino acid
                    (C) STRANDEDNESS: single
                    (D) TOPOLOGY: linear (ii) MOLECULE TYPE: protein (xi) SEQUENCE DESCRIPTION: SEQ ID NO: 3:

Leu Ser Pro Tyr Ser Ser Asp Thr Thr Pro Cys Cys Phe Ala Tyr Ile
1               5                   10                  15

Ala Arg Pro Leu Pro Arg Ala His Ile Lys Glu Tyr Phe Tyr Thr Ser
                20                  25                  30

Gly Lys Cys Ser Asn Pro Ala Val Val Phe Val Thr Arg Lys Asn Arg
            35                  40                  45

Gln Val Cys Ala Asn Pro Glu Lys Lys Trp Val Arg Glu Tyr Ile Asn
        50                  55                  60

Ser Leu Glu Met Ser
65

(2) INFORMATION FOR SEQ ID NO: 4:

(i) SEQUENCE CHARACTERISTICS:
                    (A) LENGTH: 69 amino acids
                    (B) TYPE: amino acid
                    (C) STRANDEDNESS: single
                    (D) TOPOLOGY: linear (ii) MOLECULE TYPE: protein (xi) SEQUENCE DESCRIPTION: SEQ ID NO: 4:

Gln Ser Pro Tyr Ser Ser Asp Thr Thr Pro Cys Cys Phe Ala Tyr Ile
1               5                   10                  15

Ala Arg Pro Leu Pro Arg Ala His Ile Lys Glu Tyr Phe Tyr Thr Ser
                20                  25                  30

Gly Lys Cys Ser Asn Pro Ala Val Val Phe Val Thr Arg Lys Asn Arg
            35                  40                  45

Gln Val Cys Ala Asn Pro Glu Lys Lys Trp Val Arg Glu Tyr Ile Asn
        50                  55                  60

Ser Leu Glu Met Ser
65

(2) INFORMATION FOR SEQ ID NO: 5:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ii) MOLECULE TYPE: cDNA (xi) SEQUENCE DESCRIPTION: SEQ ID NO: 5:

GATTGGTGGC GACGACTCCT                                                              20

(2) INFORMATION FOR SEQ ID NO: 6:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ii) MOLECULE TYPE: cDNA (xi) SEQUENCE DESCRIPTION: SEQ ID NO: 6:

```
CAACTGGTAA TGGTAGCGAC                                                    20

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

CCATGAAGGT CTCCGCGGCA C                                                  21

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CCTAGCTCAT CTCCAAAGAG                                                    20

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TTAATTAATT AAATCGATTC ATATGTCCCC ATATTCCTCG GACAC                         45

(2) INFORMATION FOR SEQ ID NO: 10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

TACTGATATA AATCTAGACT AGCTCATCTC CAAAGAGTTG                               40

(2) INFORMATION FOR SEQ ID NO: 11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CATGAAAAAA AAATGGCCAA GGCTGTCCCC GTACTCCTCC GACACCACCC CGTG              54

(2) INFORMATION FOR SEQ ID NO: 12:
```

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 12:

```
CACGGGGTGG TGTCGGAGGA GTACGGGGAC AGCCTTGGCC ATTTTTTTTT          50
```

(2) INFORMATION FOR SEQ ID NO: 13:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..276

(xi) SEQUENCE DESCRIPTION: SEQ ID NO: 13:

```
ATG AAG GTC TCC GCG GCA CGC CTC GCT GTC ATC CTC ATT GCT ACT GCC       48
Met Lys Val Ser Ala Ala Arg Leu Ala Val Ile Leu Ile Ala Thr Ala
 1               5                  10                  15

CTC TGC GCT CCT GCA TCT GCC TCC CCA TAT TCC TCG GAC ACC ACA CCC       96
Leu Cys Ala Pro Ala Ser Ala Ser Pro Tyr Ser Ser Asp Thr Thr Pro
             20                  25                  30

TGC TGC TTT GCC TAC ATT GCC CGC CCA CTG CCC CGT GCC CAC ATC AAG      144
Cys Cys Phe Ala Tyr Ile Ala Arg Pro Leu Pro Arg Ala His Ile Lys
         35                  40                  45

GAG TAT TTC TAC ACC AGT GGC AAG TGC TCC AAC CCA GCA GTC GTC TTT      192
Glu Tyr Phe Tyr Thr Ser Gly Lys Cys Ser Asn Pro Ala Val Val Phe
     50                  55                  60

GTC ACC CGA AAG AAC CGC CAA GTG TGT GCC AAC CCA GAG AAG AAA TGG      240
Val Thr Arg Lys Asn Arg Gln Val Cys Ala Asn Pro Glu Lys Lys Trp
 65                  70                  75                  80

GTT CGG GAG TAC ATC AAC TCT TTG GAG ATG AGC TAG G                    277
Val Arg Glu Tyr Ile Asn Ser Leu Glu Met Ser  *
                 85                  90
```

(2) INFORMATION FOR SEQ ID NO: 14:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Lys Val Ser Ala Ala Arg Leu Ala Val Ile Leu Ile Ala Thr Ala
 1               5                  10                  15

Leu Cys Ala Pro Ala Ser Ala Ser Pro Tyr Ser Ser Asp Thr Thr Pro
             20                  25                  30

Cys Cys Phe Ala Tyr Ile Ala Arg Pro Leu Pro Arg Ala His Ile Lys
         35                  40                  45

Glu Tyr Phe Tyr Thr Ser Gly Lys Cys Ser Asn Pro Ala Val Val Phe
     50                  55                  60

Val Thr Arg Lys Asn Arg Gln Val Cys Ala Asn Pro Glu Lys Lys Trp
```

```
                65                  70                  75                  80
           Val Arg Glu Tyr Ile Asn Ser Leu Glu Met Ser
                           85                  90
```

(2) INFORMATION FOR SEQ ID NO: 15:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

```
CGATTCGAAC TTCTCGATTC GAACTTCTGA TAGACTTCGA AATTAATACG ACTCACTATA    60

GGGAGA                                                                66
```

(2) INFORMATION FOR SEQ ID NO: 16:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
CCACAACGGT TTCCCTCTAG AAATAATTTT GTTTAACTTT AAGAAGGAGA TATACATATG    60

GCTAGAATT                                                             69
```

(2) INFORMATION FOR SEQ ID NO: 17:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..51

(xi) SEQUENCE DESCRIPTION: SEQ ID NO: 17:

```
CGC GCC CGG GGA TCC TCT AGA GTC GAC CTG CAG CCC AAG CTT ATC ATC    48
Arg Ala Arg Gly Ser Ser Arg Val Asp Leu Gln Pro Lys Leu Ile Ile
          95                  100                 105

GAT                                                                51
Asp
```

(2) INFORMATION FOR SEQ ID NO: 18:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 18:

```
Arg Ala Arg Gly Ser Ser Arg Val Asp Leu Gln Pro Lys Leu Ile Ile
 1               5                  10                  15
Asp
```

(2) INFORMATION FOR SEQ ID NO: 19:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:2..232

(xi) SEQUENCE DESCRIPTION: SEQ ID NO: 19:

```
C ATG AAA AAA AAA TGG CCA AGG CTG TCC CCG TAC TCC TCC GAC ACC         46
  Met Lys Lys Lys Trp Pro Arg Leu Ser Pro Tyr Ser Ser Asp Thr
       20                  25                  30

ACC CCG TGC TGC TTT GCC TAC ATT GCC CGC CCA CTG CCC CGT GCC CAC       94
Thr Pro Cys Cys Phe Ala Tyr Ile Ala Arg Pro Leu Pro Arg Ala His
         35                  40                  45

ATC AAG GAG TAT TTC TAC ACC AGT GGC AAG TGC TCC AAC CCA GCA GTC      142
Ile Lys Glu Tyr Phe Tyr Thr Ser Gly Lys Cys Ser Asn Pro Ala Val
         50                  55                  60

GTC TTT GTC ACC CGA AAG AAC CGC CAA GTG TGT GCC AAC CCA GAG AAG      190
Val Phe Val Thr Arg Lys Asn Arg Gln Val Cys Ala Asn Pro Glu Lys
 65                  70                  75                  80

AAA TGG GTT CGG GAG TAC ATC AAC TCT TTG GAG ATG AGC TAA              232
Lys Trp Val Arg Glu Tyr Ile Asn Ser Leu Glu Met Ser *
             85                  90

AGCTTGCGGC CGCACTCG                                                  250
```

(2) INFORMATION FOR SEQ ID NO: 20:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Lys Lys Lys Trp Pro Arg Leu Ser Pro Tyr Ser Ser Asp Thr Thr
 1               5                  10                  15

Pro Cys Cys Phe Ala Tyr Ile Ala Arg Pro Leu Pro Arg Ala His Ile
             20                  25                  30

Lys Glu Tyr Phe Tyr Thr Ser Gly Lys Cys Ser Asn Pro Ala Val Val
         35                  40                  45

Phe Val Thr Arg Lys Asn Arg Gln Val Cys Ala Asn Pro Glu Lys Lys
     50                  55                  60

Trp Val Arg Glu Tyr Ile Asn Ser Leu Glu Met Ser
 65                  70                  75
```